US008741568B2

(12) United States Patent
Corless et al.

(10) Patent No.: US 8,741,568 B2
(45) Date of Patent: Jun. 3, 2014

(54) DETECTION OF HUMAN PAPILLOMAVIRUS

(75) Inventors: Caroline Corless, Liverpool (GB); Malcolm Guiver, Salisbury (GB)

(73) Assignee: Health Protection Agency, Salisbury (GB)

( * ) Notice: Subject to any disclaimer, the term of this patent is extended or adjusted under 35 U.S.C. 154(b) by 692 days.

(21) Appl. No.: 12/526,462

(22) PCT Filed: Feb. 8, 2008

(86) PCT No.: PCT/GB2008/050080
§ 371 (c)(1),
(2), (4) Date: Jan. 6, 2010

(87) PCT Pub. No.: WO2008/096177
PCT Pub. Date: Aug. 14, 2008

(65) Prior Publication Data
US 2010/0143885 A1    Jun. 10, 2010

(30) Foreign Application Priority Data

Feb. 9, 2007 (GB) .................................. 0702557.0

(51) Int. Cl.
*C12Q 1/68* (2006.01)
*C12P 19/34* (2006.01)
*C07H 21/04* (2006.01)

(52) U.S. Cl.
USPC ........ 435/6.12; 435/6.1; 435/6.11; 536/24.33

(58) Field of Classification Search
None
See application file for complete search history.

(56) References Cited

U.S. PATENT DOCUMENTS

| | | | | |
|---|---|---|---|---|
| 5,447,839 | A * | 9/1995 | Manos et al. ...................... | 435/5 |
| 5,527,898 | A * | 6/1996 | Bauer et al. ................... | 536/24.3 |
| 7,670,774 | B2 * | 3/2010 | Moon et al. ................... | 435/6.14 |
| 2002/0137021 | A1* | 9/2002 | Kroeger et al. .................... | 435/5 |
| 2003/0165821 | A1 | 9/2003 | Van Doorn et al. | |
| 2004/0146910 | A1 | 7/2004 | Zhou | |
| 2004/0248085 | A1* | 12/2004 | Lee et al. ........................... | 435/5 |
| 2005/0026164 | A1 | 2/2005 | Zhou | |
| 2005/0175989 | A1* | 8/2005 | Lin et al. ........................... | 435/5 |
| 2005/0244851 | A1 | 11/2005 | Blume et al. | |

FOREIGN PATENT DOCUMENTS

| | | |
|---|---|---|
| EP | 1403384 | 3/2004 |
| EP | 08 709 600.4-2402 | 7/2011 |
| WO | WO 95/22626 | 8/1995 |
| WO | 02/103050 | 12/2002 |
| WO | WO 03/083142 | 10/2003 |
| WO | WO 2004094666 A1 * | 11/2004 |
| WO | 2006/038753 | 4/2006 |
| WO | WO 2007130519 A2 * | 11/2007 |
| WO | PCT/GB2008/050080 | 8/2008 |
| WO | PCT/GB2008/050080 | 6/2009 |

OTHER PUBLICATIONS

Huang, S-L. et al., "Comparison between the hybrid capture II test and an SPF1/GP6+ PCR-Based assay for detection of human papillomavirus DNA in cervical swab samples", Journal of Clinical Microbiology, vol. 44, No. 5, pp. 1733-1739, (2006).
Gravitt, P. E. et al., "Improved amplification of genital human papillomaviruses", Journal of Clinical Microbiology, vol. 38, No. 1, pp. 357-361, (2000).
Hart, K. W. et al., "Novel Method for detection, typing, and quantification of human papillomaviruses in clinical samples", Journal of Clinical Microbiolgy, vol. 39, No. 9, pp. 3204-3212. (2001).
Jiang, H. et al., "Genotyping of human papillomavirus in cervical lesions by L1 consensus PCR and the Luminex xMAP system", Journal of Medical Microbiology, vol. 55, pp. 715-720, (2006).
Lin, C. et al., Database EMBL, EBI Database Accession No. AEB55781, "HPV6 probe SEQ ID No. 5", abstract, (2005).
Lin, C. et al., Database EMBL, EBI Database Accession No. AER43584, "HPV6 L1 gene specific probe", abstract, 2 pages, (2007).
Moon, W. et al., Database EMBL, EBI Database Accession No. AEG92035, "HPV DNA probe 16L1", abstract, (2006).
Schmitt, M. et al., "Bead-based multiplex genotyping of human papillomaviruses", Journal of Clinical Microbiology, vol. 44, No. 2, pp. 504-512, (2006).
Ting, Y. et al., Database EMBL, EBI Database Accession No. AAQ98589, "HPV16 specific oligonucleotide probe MY96", abstract, (1996).
Wallace, J. et al., "Facile, comprehensive, high-throughput genotyping of human genital papillomaviruses using spectrally addressable liquid bead microarrays", Journal of Molecular Diagnostics, vol. 7, No. 1, pp. 72-80, (2001).
UK Search Report for Application No. GB0702557.0 dated Jun. 11, 2007.
International Search Report dated Aug. 12, 2008 for Application No. PCT/GB2008/050080.

* cited by examiner

*Primary Examiner* — Young J Kim
(74) *Attorney, Agent, or Firm* — Evan Law Group LLC

(57) ABSTRACT

There is provided an in vitro method of detecting human papillomavirus nucleic acid in a sample, comprising: (a) contacting said sample with forward and reverse oligonucleotide primers, wherein said primers bind to target sites in the human papillomavirus L1 gene, or the complement thereof, under conditions suitable to promote amplification of a portion of said human papillomavirus L1 gene or complement, thereby generating an amplicon; (b) contacting said amplicon with a probe, wherein the probe binds to a target site within said amplicon; and (c) detecting binding of said probe to said amplicon; wherein said forward primer binds to a target site having the sequence SEQ ID NO: 1; and wherein said reverse primer binds to a target site having the sequence SEQ ID NO: 2.

28 Claims, 1 Drawing Sheet

|  | Type | 16 | 18 | 31 | 33 | 35 | 39 | 45 | 51 | 52 | 53 | 56 | 58 | 59 | 66 | 68 | 73 | 6 | 11 | Luminex result |
|---|---|---|---|---|---|---|---|---|---|---|---|---|---|---|---|---|---|---|---|---|
| Luminex HPV genotype probe (MFI) | 16 | 6596 | 222 | 265 | 277 | 225 | 298 | 178 | 258 | 340 | 287 | 241 | 278 | 372 | 341 | 289 | 227 | 136 | 260 | 16 |
| | 18 | 189 | 5046 | 312 | 237 | 328 | 367 | 296 | 192 | 228 | 198 | 285 | 208 | 307 | 368 | 390 | 366 | 351 | 387 | 18 |
| | 31 | 269 | 211 | 2314 | 277 | 328 | 267 | 248 | 273 | 209 | 195 | 346 | 317 | 341 | 360 | 498 | 242 | 246 | 533 | 31 |
| | 31 | 269 | 211 | 2877 | 357 | 339 | 223 | 284 | 243 | 316 | 218 | 319 | 247 | 268 | 323 | 344 | 300 | 292 | 390 | 31 |
| | 33 | 252 | 219 | 363 | 4823 | 315 | 223 | 284 | 243 | 114 | 295 | 278 | 397 | 351 | 260 | 461 | 264 | 273 | 427 | 33 |
| | 33 | 227 | 242 | 325 | 5501 | 274 | 307 | 256 | 219 | 198 | 186 | 273 | 218 | 255 | 308 | 468 | 250 | 260 | 525 | 33 |
| | 35 | 274 | 279 | 371 | 362 | 2510 | 469 | 257 | 223 | 239 | 237 | 393 | 323 | 593 | 296 | 1459 | 321 | 360 | 689 | 35 |
| | 39 | 341 | 218 | 208 | 235 | 367 | 4269 | 182 | 167 | 195 | 305 | 257 | 221 | 240 | 400 | 295 | 274 | 260 | 388 | 39 |
| | 45 | 256 | 208 | 329 | 284 | 309 | 288 | 3848 | 210 | 209 | 278 | 233 | 342 | 326 | 466 | 415 | 362 | 424 | 682 | 45 |
| | 45 | 323 | 446 | 344 | 242 | 380 | 271 | 8132 | 206 | 264 | 295 | 282 | 322 | 338 | 393 | 276 | 253 | 351 | 741 | 45 |
| | 51 | 144 | 154 | 291 | 287 | 297 | 243 | 304 | 6455 | 244 | 120 | 410 | 238 | 431 | 296 | 1147 | 244 | 266 | 565 | 51 |
| | 52 | 371 | 235 | 305 | 261 | 370 | 264 | 260 | 238 | 5320 | 231 | 586 | 224 | 473 | 362 | 391 | 236 | 241 | 365 | 52 |
| | 53 | 173 | 246 | 274 | 246 | 315 | 231 | 209 | 256 | 369 | 6937 | 193 | 258 | 297 | 360 | 307 | 258 | 316 | 594 | 53 |
| | 53 | 239 | 193 | 248 | 226 | 180 | 258 | 253 | 161 | 150 | 5716 | 368 | 170 | 292 | 214 | 236 | 180 | 172 | 325 | 54 |
| | 56 | 306 | 185 | 256 | 301 | 251 | 209 | 263 | 243 | 199 | 305 | 11815 | 300 | 286 | 269 | 384 | 174 | 331 | 472 | 56 |
| | 56 | 305 | 292 | 365 | 3230 | 579 | 392 | 354 | 276 | 246 | 406 | 13142 | 301 | 686 | 395 | 431 | 449 | 321 | 786 | 56 |
| | 58 | 352 | 285 | 362 | 468 | 408 | 293 | 304 | 247 | 223 | 262 | 344 | 5740 | 550 | 387 | 449 | 351 | 322 | 724 | 58 |
| | 58 | 297 | 317 | 433 | 551 | 457 | 360 | 346 | 385 | 259 | 317 | 409 | 7601 | 627 | 354 | 409 | 407 | 324 | 721 | 58 |
| | 59 | 365 | 295 | 332 | 313 | 492 | 349 | 308 | 285 | 296 | 209 | 430 | 360 | 6654 | 442 | 367 | 570 | 371 | 301 | 59 |
| | 66 | 248 | 237 | 232 | 245 | 256 | 175 | 185 | 201 | 310 | 232 | 2843 | 280 | 262 | 4950 | 71 | 287 | 264 | 498 | 66 |
| | 66 | 166 | 169 | 267 | 259 | 332 | 231 | 213 | 85 | 311 | 206 | 2904 | 214 | 250 | 4957 | 329 | 214 | 243 | 474 | 66 |
| | 68 | 304 | 203 | 265 | 262 | 293 | 176 | 291 | 269 | 196 | 226 | 188 | 239 | 242 | 334 | 11851 | 323 | 297 | 660 | 68 |
| | 73 | 246 | 253 | 331 | 275 | 305 | 251 | 357 | 236 | 185 | 245 | 327 | 291 | 332 | 333 | 403 | 5332 | 325 | 736 | 73 |

DETECTION OF HUMAN PAPILLOMAVIRUS

The present invention relates to detection of papillomavirus, in particular, human papillomavirus, and to reagents and kits therefor.

Papillomaviruses are a diverse group of double stranded DNA viruses that infect the skin and mucous membranes of humans and a variety of animals.

There are more than 100 different genotypes of human papillomavirus (HPV), of which 30 are found in the anogenital tract. Some HPV genotypes cause benign skin warts or papillomas, after which the virus family is named. HPV infection associated with the development of common warts is transmitted environmentally or by casual skin-to-skin contact.

HPV infection may be transmitted through sexual intercourse. Genital or anal warts are the most easily recognised sign of genital HPV infection. Genital HPV infection is very common, with estimates suggesting that up to 75% of women will become infected with one or more sexually-transmitted HPV genotypes at some point during adulthood.

HPV genotypes are divided into "low" and "high" risk genotypes. "Low" risk genotypes include genotype 5, 6 and 11. Genotype 5 may establish infections that persist for the lifetime of an individual without ever manifesting any clinical symptoms. Genotypes 6 and 11 have been associated with about 90% of cases of genital warts, but are rarely associated with cancers. HPV genotypes 6 and 11 have also been associated with a rare condition known as recurrent respiratory papillomatosis, in which warts form on the larynx or other areas of the respiratory tract.

"High" risk genotypes (eg. genotypes 16, 18, 31, 33, 35, 39, 45, 51, 52, 53, 56, 58, 59, 66, 68, 69, 73 and 82) are known as "high risk" genotypes, because they are frequently found in cancers, in particular, cervical cancer. In this regard, infection with one or more "high" risk HPV genotypes has been identified in almost 100% of all cervical cancers, and genotypes 16 and 18 in particular have been identified in over 70% of cervical cancers. Cervical cancer kills nearly 250,000 women per year worldwide.

GenBank Accession numbers have been allocated to the HPV genotypes:

| HPV genotype | Accession Number(s) |
| --- | --- |
| HPV 6 | AF092932 |
| HPV 11 | AF335603; AF548815 |
| HPV 16 | AF536180; DQ469930; DQ680078; AF536180 |
| HPV 18 | DQ059013; AY863165; U45890; AF548846; AF548845; AF548844; AF548840; AF548837 |
| HPV 26 | X74472 |
| HPV 31 | J04353 |
| HPV 33 | U45895 |
| HPV 35 | M74117 |
| HPV 39 | M62849; U45905 |
| HPV 45 | DQ080002 |
| HPV 51 | M62877 |
| HPV 52 | DQ057316 |
| HPV 53 | X74482 |
| HPV 55 | U31791 |
| HPV 56 | X74483 |
| HPV 58 | U45928 |
| HPV 59 | X77858 |
| HPV 66 | U31794 |
| HPV 67 | Y12207; U12492 |
| HPV 68 | U46934; AJ831567; AJ831568 |
| HPV 69 | AB027020; U12497 |

-continued

| HPV genotype | Accession Number(s) |
| --- | --- |
| HPV 70 | U22461 |
| HPV 73 | X94165 |
| HPV 82 | AJ831565 |

On 8$^{th}$ Jun. 2006, the US FDA approved Gardasil, a prophylactic HPV vaccine developed by Merck. The vaccine protects women against initial infection with HPV genotypes 6, 11, 16 and 18.

As this, and similar, vaccine programs get underway, comprehensive HPV detection and typing assays will be essential to assess their efficacy in eradicating HPV in a previously infected patient, or in preventing HPV infection.

HPV is a particularly difficult virus to study from an epidemiologic standpoint. In this regard, there has been only very limited success in propagating HPV in the laboratory, and the exclusive species specificity of HPV also limits the ability to propagate HPV in animal models. Furthermore, HPV is only weakly antigenic, and the immune response to the virus is variable among individuals. In addition, viral subtyping is problematic with these techniques, since the capsid proteins of different HPV subtypes are antigenically quite similar.

The cervical Papanicolaou (Pap) smear is one of the most effective indicators of common and potentially serious clinical manifestations of HPV infection. Abnormalities delineated by Pap smear that suggest HPV cytopathy or cervical dysplasia are further evaluated by colposcopy and optionally biopsy.

Due to difficulties associated with in vitro culture of HPV, identification of HPV infection is dependant on detecting HPV DNA in a sample.

The HPV genome is organised into "early" genes (E1, E2, E4, E5, E6 and E7) and "late" genes (L1 and L2—coding for major and minor capsid proteins respectively). The L1 (major capsid protein) gene has been widely studied as a target for HPV detection and genotyping.

Tests for detecting and optionally typing HPV using nucleic acid probes have been commercially available since the late 1980s. By way of example, known methods for detecting HPV DNA include Southern blot, dot blot, reverse line blot, ELISA and in situ hybridization techniques, with signal and/or target nucleic acid amplification, most notably using the polymerase chain reaction (PCR).

However, early tests did not achieve widespread use because they were not capable of detecting all oncogenic HPV genotypes and suffered from low sensitivity and/or specificity. In this regard, a significant heterogeneity has been identified at the nucleotide level between the different HPV genotypes, which has hindered the development of a simple universal test for detection of all HPV genotypes.

A further problem associated with these known methods is that they cannot easily be automated or deployed on a high-throughput platform, and are thus unsuitable when there is a large volume of patients.

PCR has been used for HPV detection, genotyping and viral load determination. General or consensus primer-mediated PCR assays have enabled screening for a broad spectrum of HPV types in clinical specimens using a single PCR reaction. Using consensus primers in a real-time quantitative PCR test (RQ-PCR), it is possible to generate viral load (concentration) data from reaction curves generated by monitoring PCR reaction kinetics in real time.

One commercially available HPV DNA detection test is the Hybrid Capture® 2 HPV DNA test (Digene Corporation), which has been used as an adjunct to Pap smear testing for women, and may be ordered in response to abnormal Pap smear results. Hybrid Capture® technology relies on hybridisation of RNA probes to target DNA, capture of the DNA-RNA hybrid using a labelled antibody, and signal amplification. The Hybrid Capture® 2 test detects 5 low risk and 13 high risk HPV genotypes.

A disadvantage of the Hybrid Capture® 2 HPV DNA test is the high false-positive rate—which is as high as 17% under typical operating conditions.

A number of HPV genotyping assays have recently been described that employ Luminex xMAP liquid bead microarray, flow cytometry technology (Luminex Corporation, Austin, Tex.).

The Luminex xMAP technology allows simultaneous detection of up to 100 different PCR amplified gene targets in a single reaction (multiplexing). The Luminex system employs uniquely identified sets of microspheres, each set having a unique spectral signature (the microspheres are internally dyed with mixtures of red and infrared fluorophores) and a different, specific, oligonucleotide probe bound to the surface (within each microsphere set, the attached probes are the same).

In use of the Luminex technology, the uniquely identifiable microsphere sets (with attached probes) are combined with biotin-labelled PCR-amplified target nucleic acid sequences, to form target nucleic acid-probe-microsphere hybrids. A fluorescent dye-labelled conjugate (eg. streptavidin R-phycoerythrin) is added to the reaction at this stage and binds to the bound target nucleic acid molecule.

Injecting this mixture into the Luminex 100™ instrument aligns the microspheres in single file prior to passing the microspheres through a detection chamber. Lasers illuminate the red and infrared dyes of the microspheres, thereby allowing classification of the microspheres to one of the microsphere sets. Lasers also excite the fluorescent label associated with the bound target nucleic acid. The colour signals are captured in real time, and the fluorescent intensity of the reporter molecule is used to measure the quantity of target nucleic acid molecules attached to each set of the microspheres.

A disadvantage of these known HPV Luminex assays is their poor sensitivity.

There is, therefore, a need to provide an alternative and/or improved system for detecting human papillomavirus.

Accordingly, the present invention provides an in vitro method of detecting human papillomavirus nucleic acid in a sample, comprising (i) contacting said sample with forward and reverse oligonucleotide primers, wherein said primers bind to target sites in the human papillomavirus L1 gene, or the complement thereof, under conditions suitable to promote amplification of a portion of said human papillomavirus L1 gene or complement, thereby generating an amplicon; (ii) contacting said amplicon with a probe, wherein the probe binds to a target site within said amplicon; and (iii) detecting binding of said probe to said amplicon; wherein said forward primer binds to a target site having the sequence SEQ ID NO: 1; and wherein said reverse primer binds to a target site having the sequence SEQ ID NO: 2.

The present invention further provides an in vitro method of detecting human papillomavirus nucleic acid in a sample, comprising: (i) contacting said sample with at least one oligonucleotide probe, wherein the probe binds a target site within the human papillomavirus L1 gene, or the complement thereof; and (ii) detecting binding of said probe to said target site; wherein said probe comprises a nucleic acid sequence having at least 85%, preferably at least 90%, preferably at least 95%, most preferably 100% sequence identity to a nucleic acid sequence selected from SEQ ID NO: 15, SEQ ID NO: 16, SEQ ID NO: 17, SEQ ID NO: 18, SEQ ID NO: 19, SEQ ID NO: 20, SEQ ID NO: 21 SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

In the field of detecting and diagnosing sexually transmitted diseases, it is particularly important to keep the incidence of "false positive" results as low as possible due to the sensitive nature of the test results for the patient, cost and implications of inappropriate treatment, and the legal implications of providing an incorrect result.

Advantageously, the method of the present invention provides improved specificity and sensitivity compared to existing tests for detecting human papillomavirus.

In one aspect, the detection assay of the present invention enables detection and identification of up to 20 HPV genotypes in a single hybridisation reaction taking approximately 1 hour.

A sample may be for instance, a food, sewerage, environmental, veterinary or clinical sample. Clinical samples may include urethral swabs, vaginal swabs, cervical swabs, rectal swabs, penile swabs, throat/oral swabs, respiratory tract samples, urine, blood, cerebrospinal fluid, liquid based cytology samples, tissue biopsies and any other samples from humans.

Suitable probes for use in the present invention bind specifically to human papillomavirus nucleic acid. Thus, suitable probes may be oligonucleotides, or may be protein ligands, for example, antibodies.

It is preferred that the probes are oligonucleotide probes, which bind to their target sites within the human papillomavirus nucleic acid by way of complementary base-pairing. For the avoidance of doubt, in the context of the present invention, the definition of an oligonucleotide probe does not include the full length L1 gene (or the complement thereof).

In the context of the present invention, the term "isolated", when applied to a polynucleotide, denotes that the polynucleotide has been removed from its natural genetic milieu and is thus free of other extraneous or unwanted coding sequences.

Probes are designed to bind to the target gene sequence based on a selection of desired parameters, using conventional software. It is preferred that the binding conditions are such that a high level of specificity is provided—ie. binding occurs under "stringent conditions". In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence binds to a perfectly matched probe. In this regard, the $T_m$ of probes of the present invention, at a salt concentration of about 0.02M or less at pH 7, is preferably above 40° C. and preferably below 70° C., more preferably about 53° C. Premixed binding solutions are available (eg. EXPRESSHYB Hybridisation Solution from CLONTECH Laboratories, Inc.), and binding can be performed according to the manufacturer's instructions. Alternatively, one of a skill in the art can devise variations of these binding conditions.

Following binding, washing under stringent (preferably highly stringent) conditions removes unbound nucleic acid molecules. Typical stringent washing conditions include washing in a solution of 0.5-2×SSC with 0.1% SDS at 55-65° C. Typical highly stringent washing conditions include washing in a solution of 0.1-0.2×SSC with 0.1% SDS at 55-65° C. A skilled person can readily devise equivalent conditions for example, by substituting SSPE for the SSC in the wash solution.

Apart from the stringency of the hybridization conditions, hybridization specificities may be affected by a variety of probe design factors, including the overall sequence similarity, the distribution and positions of mismatching bases, and the amount of free energy of the DNA duplexes formed by the probe and target sequences.

It is preferable to screen the probes to minimise self-complementarity and dimer formation (probe-probe binding). Preferred probes of the present invention are selected so as to have minimal homology with human DNA. The selection process may involve comparing a candidate probe sequence with human DNA and rejecting the probe if the homology is greater than 50%. The aim of this selection process is to reduce annealing of probe to contaminating human DNA sequences and hence allow improved specificity of the assay.

In one aspect, the oligonucleotide probe is 1-40 nucleotides long. Preferably, the probe is at least 10 nucleotides long, preferably at least 15, most preferably at least 20 nucleotides long, and preferably the probe is up to 35 nucleotides long, more preferably up to 30 nucleotides long, most preferably up to 26 nucleotides long. Thus, in one aspect, the probe is 20-26 nucleotides long. It is an advantage to use short probes, as this enables faster annealing to target human papillomavirus nucleic acid.

The "complement" of a nucleic acid sequence binds via complementary base-pairing to said nucleic acid sequence. A non-coding (anti-sense) nucleic acid strand is also known as a "complementary strand", because it binds via complementary base-pairing to a coding (sense) strand.

Thus, in one aspect, the probe binds to a target sequence within the coding (sense) strand of the target human papillomavirus nucleic acid. Alternatively, in another aspect, the probe binds to a target sequence within the complementary, non-coding (anti-sense) strand of the target human papillomavirus nucleic acid.

The target site to which the probe binds may be about 1-40 nucleotides long, preferably about 15-30 nucleotides long and most preferably about 20-26 nucleotides long.

The target site to which the probe binds is located within the human papillomavirus L1 gene, or within the complement thereof. In one aspect, the target site to which the probe binds is located within an amplicon generated by amplification of a portion of the human papillomavirus L1 gene that includes the target site (or the complement thereof). Binding of the probe indicates that the sample contains human papillomavirus nucleic acid.

The probe preferably binds to a target site that includes a known human papillomavirus genotype-specific polymorphism—ie. the target sequence includes a nucleic acid sequence that is unique to a specific genotype of human papillomavirus. Binding of the probe indicates that the sample contains human papillomavirus nucleic acid including the known genotype-specific polymorphism, and enables identification of the human papillomavirus genotype in the sample.

In this regard, there is significant heterogeneity between the L1 genes of the different human papillomavirus genotypes.

Thus, in one aspect, the probes are genotype-specific probes. Preferably, the genotype-specific polymorphism is associated with a "low risk" genotype of HPV (eg. genotypes 6 or 11) or a "high risk" genotype of HPV (eg. genotypes 16, 18, 31, 33, 35, 39, 45, 51, 52, 53, 56, 58, 59, 66, 68, 69, 73 and 82).

In this regard, good results have been obtained using one or more probes selected from genotype-specific probes SEQ ID NOs: 15-34, as shown in Table 1 below.

TABLE 1

| PROBE SEQ ID NO: | GENOTYPE DETECTED | SEQUENCE: |
|---|---|---|
| 15 | HPV-6 | CATCTTCCACATACACCAATT |
| 16 | HPV-11 | CACTAATTCAGATTATAAGGAATACA |
| 17 | HPV-16 | GCCATATCTACTTCAGAAACT |
| 18 | HPV-18 | ATTTAAGCAGTATAGCAGACA |
| 19 | HPV-31 | AATTGCAAACAGTGATACTAC |
| 20 | HPV-33 | GACTTTATGCACACAAGTAACTA |
| 21 | HPV-35 | TGTAGTTGATACAACCCGTAG |
| 22 | HPV-39 | CTACCTCTATAGAGTCTTCCAT |
| 23 | HPV-45 | TGTGCCTCTACACAAAATCCT |
| 24 | HPV-51 | GTTTCCCCAACATTTACTCCA |
| 25 | HPV-53 | GATACCACCAGGAATACAAAC |
| 26 | HPV-58 | CACTGAAGTAACTAAGGAAGGT |
| 27 | HPV-59 | TATTCCTAATGTATACACACCT |
| 28 | HPV-66 | GATGCCCGTGAAATCAATCAA |
| 29 | HPV-68 | TAAGGAATATATTAGGCATGT |
| 30 | HPV-69 | TCACTATTAGTACTGTATCTG |
| 31 | HPV-73 | ACAACGTATGCCAACTCTAAT |
| 32 | HPV-82 | TGCACAGACATTCACTCCAAC |
| 33 | HPV-52 | GAGGTTAAAAAGGAAAGCACA |
| 34 | HPV-56 | CAGAACAGTTAAGTAAATATG |

It will, however, be appreciated that variants may be employed, which differ from the above-mentioned probe sequences by one or more nucleotides. In this regard, conservative substitutions are preferred.

Thus, in one aspect, the probe comprises a nucleic acid sequence having at least 85%, preferably at least 90%, 91%, 92%, 93%, 94%, 95%, 96%, 97%, 98%, 99% and most preferably 100% sequence identity to a nucleic acid sequence selected from SEQ ID NO: 15, SEQ ID NO: 16, SEQ ID NO: 17, SEQ ID NO: 18, SEQ ID NO: 19, SEQ ID NO: 20, SEQ ID NO: 21 SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

In one aspect, the probe consists of a nucleic acid sequence having at least 85%, preferably at least 90%, 91%, 92%, 93%, 94%, 95%, 96%, 97%, 98%, 99% and most preferably 100% sequence identity to a nucleic acid sequence selected from SEQ ID NO: 15, SEQ ID NO: 16, SEQ ID NO: 17, SEQ ID NO: 18, SEQ ID NO: 19, SEQ ID NO: 20, SEQ ID NO: 21 SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

An alternative means for defining variant probe sequences is by defining the number of nucleotides that differ between the variant sequence and the specific probe sequence. In this regard, the present invention embraces variant probe sequences that differ from SEQ ID NO: 15, 16, 17, 18, 19, 20, 21, 22, 23, 24, 25, 26, 27, 28, 29, 30, 31, 32, 33 or 34 at no more than 5 nucleotide positions, preferably at no more than 4, 3 or 2 nucleotide positions, most preferably at no more than 1 nucleotide position.

In one aspect, prior to detecting binding of human papillomavirus nucleic acid to said probe, any unbound human papillomavirus nucleic acid is separated from the bound human papillomavirus nucleic acid. Unbound human papillomavirus nucleic acid is preferably removed by washing, under stringent (preferably highly stringent) conditions.

In one aspect, the probe may be immobilised onto a support or platform. Immobilising the probe provides a physical location for the probe, and may serve to fix the probe at a desired location and/or facilitate recovery or separation of probe.

The support may be a rigid solid support made from, for example, glass or plastic, or else the support may be a membrane, such as nylon or nitrocellulose membrane. 3D matrices are suitable supports for use with the present invention—eg. polyacrylamide or PEG gels.

In one embodiment, the support may be in the form of one or more beads or microspheres, for example in the form of a liquid bead microarray. Suitable beads or microspheres are available commercially (eg. Luminex Corp., Austin, Tex.). The surfaces of the beads may be carboxylated for attachment of DNA. The beads or microspheres may be uniquely identified, thereby enabling sorting according to their unique features (for example, by bead size or colour, or a unique label). In one aspect, the beads/microspheres are internally dyed with fluorophores (eg. red and/or infrared fluorophores) and can be distinguished from each other by virtue of their different fluorescent intensity.

The probes may be immobilised to the support/platform by a variety of means. By way of example, probes may be immobilised onto a support such as a nylon membrane by UV cross-linking. Biotin-labelled probes may be bound to streptavidin-coated substrates, and probes prepared with amino linkers may be immobilised onto silanised surfaces.

Another means of immobilising a probe is via a poly-T tail or a poly-C tail, for example at the 3' or 5' end. A poly-T tail typically consists of a run of from 1 to 100 thymine residues added to the probe (typically at the 3' end) with a terminal transferase. Preferably, from 1 to 20 thymine residues are added. A poly-C tail is typically C6, C12 or a unilinker (typically added at the 5' end of the probe). Suitable unilinkers are commercially available (eg. Operon Technologies, Inc.). The poly-T or poly-C tail is typically baked or UV cross-linked onto the solid substrate.

Addition of a poly-T or poly-C tail appears to have two functions. First, the tail increases the amount of probe that is immobilised onto the solid support. Second, the tail determines the accessibility of the probe to the target nucleic acid, and conforms the probe in such a way as to improve the efficiency of hybridisation.

Binding of the probe to the target site within the human papillomavirus L1 gene, or complement thereof (or within the amplicon derived from the L1 gene or complement) may be detected by known means. By way of example, binding of the probe to the target site may generate a detectable signal. A detectable signal may be, for example, a radioactive signal or a fluorescent signal, such as a change in fluorescence.

In one aspect, the probe is labelled with a label such as a reporter molecule, and the assay comprises detecting the label and correlating presence of label with presence of human papillomavirus nucleic acid.

In an alternative embodiment, the target human papillomavirus nucleic acid (eg. the amplicon) comprises a label, and the assay comprises detecting the label and correlating presence of label with presence of human papillomavirus nucleic acid. The label may be present in the human papillomavirus nucleic acid prior to contacting the sample with the probe. By way of example, the label may be incorporated into the human papillomavirus nucleic acid during an amplification step.

The label may comprise a detectable label such as a radio-label or a fluorescent molecule. By way of example, the label may be digoxygenin, fluorescein-isothiocyanate (FITC) or R-phycoerythrin. The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

In one aspect, the method comprises contacting said human papillomavirus nucleic acid (eg. an amplicon) with a reporter construct comprising a detectable molecule, wherein reporter construct binds to said human papillomavirus nucleic acid. Contacting the human papillomavirus nucleic acid with the reporter construct is carried out before, after or simultaneously with contacting the human papillomavirus nucleic acid with the probe. The detectable molecule component of the reporter construct may be a fluorescent molecule (such as R-phycoerythrin), or an enzyme that generates a detectable signal.

Binding of said reporter construct to the human papillomavirus nucleic acid (eg. an amplicon) may be achieved by any known means. By way of example, the reporter construct may comprise a detectably labelled oligonucleotide that hybridises with the human papillomavirus nucleic acid. Alternatively, the human papillomavirus nucleic acid may be labelled with a first attachment molecule, and said reporter construct may comprise a second attachment molecule that binds to the first attachment molecule.

Examples of attachment molecules include biotin and streptavidin. Thus, it is an option for the first attachment molecule to be biotin and for the second attachment molecule to be streptavidin (or vice versa). Other exemplary pairs of attachment molecules include receptor/ligand pairs and antibody/antigen (or hapten or epitope) pairs.

In one aspect, measuring the intensity of the detectable signal enables quantification of the amount of HPV nucleic acid in a sample, or the amount (or relative amounts) of different HPV genotypes in a sample.

In one aspect, the method comprises contacting a sample with multiple (ie. at least two) different oligonucleotide probes that bind to target sites within the human papillomavirus L1 gene, or the complement thereof (or within the amplicon), wherein each of said different probes comprises a different nucleic acid sequence, and detecting binding of said probes to said target sites.

In one aspect, the method comprises contacting said sample with at least 3, 4, 5, 6, 7, 8, 9, 10, 11, 12, 13, 14, 15, 16, 17, 18, 19 or 20 of said different probes.

This aspect of the present invention allows the simultaneous detection of multiple (ie. at least two) different HPV genotypes in a single reaction, by simultaneously detecting multiple (ie. at least two) different genotype-specific HPV nucleic acid target sequences.

Thus, in one aspect, the method comprises contacting a sample with multiple different genotype-specific probes, thereby enabling simultaneous detection of a wide spectrum of HPV genotypes—which may be present, for example, in mixed infections.

In one aspect, each of said probes comprises a different nucleic acid sequence selected from the group consisting of: (a) a nucleic acid sequence having at least 85%, preferably at least 90%, preferably at least 95%, most preferably 100% sequence identity to SEQ ID NO: 15; (b) a nucleic acid sequence having at least 85%, preferably at least 90%, preferably at least 95%, most preferably 100% sequence identity to SEQ ID NO: 16; (c) a nucleic acid sequence having at least 85%, preferably at least 90%, preferably at least 95%, most preferably 100% sequence identity to SEQ ID NO: 17; (d) a nucleic acid sequence having at least 85%, preferably at least 90%, preferably at least 95%, most preferably 100% sequence identity to SEQ ID NO: 18; (e) a nucleic acid sequence having at least 85%, preferably at least 90%, preferably at least 95%, most preferably 100% sequence identity to SEQ ID NO: 19; (f) a nucleic acid sequence having at least 85%, preferably at least 90%, preferably at least 95%, most preferably 100% sequence identity to SEQ ID NO: 20; (g) a nucleic acid sequence having at least 85%, preferably at least 90%, preferably at least 95%, most preferably 100% sequence identity to SEQ ID NO: 21; (h) a nucleic acid sequence having at least 85%, preferably at least 90%, preferably at least 95%, most preferably 100% sequence identity to SEQ ID NO: 22; (i) a nucleic acid sequence having at least 85%, preferably at least 90%, preferably at least 95%, most preferably 100% sequence identity to SEQ ID NO: 23; (j) a nucleic acid sequence having at least 85%, preferably at least 90%, preferably at least 95%, most preferably 100% sequence identity to SEQ ID NO: 24; (k) a nucleic acid sequence having at least 85%, preferably at least 90%, preferably at least 95%, most preferably 100% sequence identity to SEQ ID NO: 25; (l) a nucleic acid sequence having at least 85%, preferably at least 90%, preferably at least 95%, most preferably 100% sequence identity to SEQ ID NO: 26; (m) a nucleic acid sequence having at least 85%, preferably at least 90%, preferably at least 95%, most preferably 100% sequence identity to SEQ ID NO: 27; (n) a nucleic acid sequence having at least 85%, preferably at least 90%, preferably at least 95%, most preferably 100% sequence identity to SEQ ID NO: 28; (o) a nucleic acid sequence having at least 85%, preferably at least 90%, preferably at least 95%, most preferably 100% sequence identity to SEQ ID NO: 29; (p) a nucleic acid sequence having at least 85%, preferably at least 90%, preferably at least 95%, most preferably 100% sequence identity to SEQ ID NO: 30; (q) a nucleic acid sequence having at least 85%, preferably at least 90%, preferably at least 95%, most preferably 100% sequence identity to SEQ ID NO: 31; (r) a nucleic acid sequence having at least 85%, preferably at least 90%, preferably at least 95%, most preferably 100% sequence identity to SEQ ID NO: 32; (s) a nucleic acid sequence having at least 85%, preferably at least 90%, preferably at least 95%, most preferably 100% sequence identity to SEQ ID NO: 33; (t) a nucleic acid sequence having at least 85%, preferably at least 90%, preferably at least 95%, most preferably 100% sequence identity to SEQ ID NO: 34.

Preferably, the method employs at least four different probes, wherein each of said probes comprises a different nucleic acid sequence selected from SEQ ID NO: 15, SEQ ID NO: 16, SEQ ID NO: 17, and SEQ ID NO: 18 (or sequences having at least 85%, preferably at least 90%, preferably at least 95% sequence identity thereto). As illustrated in Table 1, above, these probes enable detection of the most common HPV genotypes—namely HPV-6 and HPV-11 (low risk), and HPV-16 and HPV-18 (high-risk), respectively.

Thus, in one aspect, the present invention enables simultaneous typing of multiple HPV genotypes in a single sample.

It is preferred to be able to distinguish the binding of one genotype-specific probe (eg. SEQ ID NO: 15) to target human papillomavirus nucleic acid from the binding of a different genotype-specific probe (eg. SEQ ID NO: 16) to target human papillomavirus nucleic acid. This enables multiple hybridisation reactions to be carried out in the same reaction vessel at the same time, and facilitates distinguishing the HPV genotypes present in the sample.

Thus, in one aspect, each different genotype-specific probe is immobilised onto a different solid support or platform, preferably onto different beads or microspheres (eg. 2, 3, 4, 5, 6, 7, 8, 9, 10, 11, 12, 13, 14, 15, 16, 17, 18, 19 or 20 different beads/microspheres). Preferably, said different solid supports or platforms are uniquely identifiable.

By way of example, the different supports (eg. beads/microspheres) may be of different sizes or colours, or may comprise a unique label. In one aspect, the different supports (eg. beads/microspheres) are dyed—such as internally dyed—with different dyes or with dyes of different fluorescent intensities. By way of example, as discussed above, different commercially available microspheres may be internally dyed with different intensities of red and/or infrared fluorophores and are thereby distinguishable from each other by their fluorescent intensity.

Hybridisation of the immobilised probes to target human papillomavirus nucleic acid (eg. an amplicon) thereby generates multiple, uniquely identifiable, target nucleic acid-probe-solid support hybrids.

In one aspect, following binding of the immobilised probes to their target sites in the human papillomavirus nucleic acid, said method further comprises sorting the supports (eg. beads/microspheres) according to their unique identification.

In one aspect, the present method makes use of Luminex liquid bead microarray, flow cytometry technology. In use of this technology, the beads/microspheres (with their bound genotype-specific probes and hybridised target nucleic acid) are aligned in single file in the Luminex 100™ instrument prior to passing the beads/microspheres through a detection chamber. Lasers illuminate the red and infrared dyes inside the microspheres, thereby allowing classification of the microspheres (and hence, allowing identification of the genotype to which the bound nucleic acid belongs).

The amount of target nucleic acid bound to each category of microsphere (ie. the amount of each genotype) may also be quantified by detecting the amount of label associated with the bound nucleic acid. In one aspect, the associated label is a fluorescent molecule (eg. R-phycoerythrin), which is excited by a laser in the Luminex 100™ instrument. The colour signals are captured in real time, and the fluorescent intensity of the label (eg. R-phycoerythrin) is used to measure the quantity of target nucleic acid molecules attached to each set of the microspheres.

Thus, in one aspect, using Luminex technology enables quantification of different HPV genotypes in a sample.

In one aspect, prior to contacting the human papillomavirus nucleic acid with said oligonucleotide probe, the method further comprises the step of amplifying a portion of the human papillomavirus L1 gene, or the complement thereof, thereby generating an amplicon.

It may be desirable to amplify the target human papillomavirus nucleic acid if the sample is small and/or comprises a heterogeneous collection of DNA sequences.

Amplification may be carried out by methods known in the art, and is preferably carried out by PCR. A skilled person would be able to determine suitable conditions for promoting amplification of a nucleic acid sequence.

Thus, in one aspect, amplification is carried out using a pair of sequence specific primers, wherein said primers bind to target sites in the human papillomavirus L1 gene, or the complement thereof, by complementary base-pairing. In the presence of a suitable DNA polymerase and DNA precursors (dATP, dCTP, dGTP and dTTP), the primers are extended, thereby initiating the synthesis of new nucleic acid strands which are complementary to the individual strands of the target nucleic acid. The primers thereby drive amplification of a portion of the human papillomavirus L1 gene, or the complement thereof, thereby generating an amplicon. This amplicon comprises the target sequence to which the probe binds.

For the avoidance of doubt, in the context of the present invention, the definition of an oligonucleotide primer does not include the full length L1 gene (or complement thereof).

The primer pair comprises forward and reverse oligonucleotide primers. A forward primer is one that binds to the complementary, non-coding (anti-sense) strand of the target nucleic acid and a reverse primer is one that binds to the corresponding coding (sense) strand of the target nucleic acid.

Primers of the present invention are designed to bind to the target gene sequence based on the selection of desired parameters, using conventional software, such as Primer Express (Applied Biosystems). In this regard, it is preferred that the binding conditions are such that a high level of specificity is provided. The melting temperature (Tm) of the primers is preferably in excess of 50° C. and is most preferably about 60° C. A primer of the present invention preferably binds to target human papillomavirus nucleic acid but is preferably screened to minimise self-complementarity and dimer formation (primer-to-primer binding).

The forward and reverse oligonucleotide primers are typically 1 to 40 nucleotides long. It is an advantage to use shorter primers, as this enables faster annealing to target nucleic acid.

Preferably the forward primer is at least 10 nucleotides long, more preferably at least 15 nucleotides long, more preferably at least 18 nucleotides long, most preferably at least 20 nucleotides long, and the forward primer is preferably up to 35 nucleotides long, more preferably up to 30 nucleotides long, more preferably up to 28 nucleotides long, most preferably up to 25 nucleotides long. In one embodiment, the forward primer is about 20-21 nucleotides long.

Preferably the reverse primers are at least 10 nucleotides long, more preferably at least 15 nucleotides long, more preferably at least 20 nucleotides long, most preferably at least 25 nucleotides long, and the reverse primers are preferably up to 35 nucleotides long, more preferably up to 30 nucleotides long, most preferably up to 28 nucleotides long. In one embodiment, the reverse primer is about 26 nucleotides long.

The amplicon is preferably in the range of 150-250 nucleotides long, preferably in the range 165-225 nucleotides long, preferably in the range 175-200 nucleotides long, and most preferably in the range 180-195 nucleotides long. In one embodiment, the amplicon is about 182-191 nucleotides long. The amplicon length will vary between different human papillomavirus genotypes, as illustrated in Table 2, below.

TABLE 2

| HPV genotype | Amplicon length (bp) |
|---|---|
| 6 | 182 |
| 11 | 182 |
| 16 | 185 |
| 18 | 188 |
| 26 | 188 |
| 31 | 185 |
| 33 | 182 |
| 35 | 185 |
| 39 | 188 |
| 45 | 188 |
| 51 | 185 |
| 52 | 182 |
| 53 | 182 |
| 55 | 188 |
| 56 | 182 |
| 58 | 182 |
| 59 | 188 |
| 66 | 182 |
| 67 | 182 |
| 68 | 188 |
| 69 | 188 |
| 70 | 188 |
| 73 | 191 |
| 82 | 188 |

The forward primer binds to a target site within the complement of the human papillomavirus L1 gene. The binding site for the forward primer comprises the sequence SEQ ID NO: 1, as illustrated in Table 3, below. In one aspect, the binding site for the forward primer consists of the sequence SEQ ID NO: 1.

The reverse primer binds to a target site within the human papillomavirus L1 gene. The binding site for the reverse primer comprises the sequence SEQ ID NO: 2, as illustrated in Table 3, below. In one aspect, the binding site for the reverse primer consists of the sequence SEQ ID NO: 2.

TABLE 3

| SEQ ID NO: 1 | CGNGTBCCDRWDTTVTTACC |
|---|---|
| SEQ ID NO: 2 | GARTWTGAHYTRCARTTTRTDTTTCA |

In this regard, it will be apparent that SEQ ID NOs: 1 and 2 are consensus sequences, wherein: H=A, C, or T; N=A, T, C, or G; W=A or T; Y=T or C, R=A or G, D=A, T, or G; B=C, T, or G; and V=G, C, or A.

In one aspect, the forward primer comprises a nucleic acid sequence having the sequence SEQ ID NO: 3, as illustrated in Table 4, below. In one aspect, the forward primer consists of a nucleic acid sequence having the sequence SEQ ID NO: 3.

In one aspect, the reverse primer comprises a nucleic acid sequence having the sequence SEQ ID NO: 9, as illustrated in Table 4, below. In one aspect, the reverse primer consists of a nucleic acid sequence having the sequence SEQ ID NO: 9.

TABLE 4

| SEQ ID NO: 3 | GCNCARGGHYWHAAYAATGG |
|---|---|
| SEQ ID NO: 9 | TGAAAHAYAAAYTGYARDTCAWAYTC |

In this regard, it will be apparent that SEQ ID NOs: 3 and 9 are consensus sequences, wherein: H=A, C, or T; N=A, T, C, or G; W=A or T; Y=T or C, R=A or G, and D=A, T, or G.

Particularly good results have been obtained using a forward primer of SEQ ID NO: 4, 5, 6, 7 or 8, as shown in Table 5 below.

TABLE 5

| Forward Primer SEQ ID NO: | SEQUENCE: |
|---|---|
| 4 | GCNCAGGGHCACATTAATGG |
| 5 | GCHCARGGHCATAACAATGG |
| 6 | GCMCAGGGYCATAATAATGG |
| 7 | GCMCAAGGYCATAATAATGG |
| 8 | GGTCAGGGTTTAAACAATGG |

In this regard, it will be apparent that SEQ ID NOs: 4-7 are consensus sequences, wherein: H=A, C, or T; N=A, T, C, or G; M=A or C; Y=T or C and R=A or G.

Particularly good results have also been obtained using a reverse primer of SEQ ID NO: 10, 11, 12, 13 or 14, as shown in Table 6 below.

TABLE 6

| Reverse Primer SEQ ID NO: | SEQUENCE: |
|---|---|
| 10 | TGAAAAATAAACTGYAAATCATATTC |
| 11 | TGAAAWATAAATTGYAAWTCATACTC |
| 12 | TGAAAMACAAACTGTAGWTCATATTC |
| 13 | TGAAAAAGAAAYTGTAAKTCATATTC |
| 14 | TGAAAWATAAAYTGYAAATCAAATTC |

In this regard, it will be apparent that SEQ ID NOs: 10-14 are consensus sequences, wherein: K=G or T; M=A or C; W=A or T; Y=T or C and R=A or G.

It will be appreciated that variants may be employed, which differ from the above-mentioned forward primer sequences by one or more nucleotides. In this regard, conservative substitutions are preferred.

Thus, in one aspect, the forward primer comprises a nucleic acid sequence having at least 85%, preferably at least 90%, 91%, 92%, 93%, 94%, 95%, 96%, 97%, 98%, 99% and most preferably 100% sequence identity to a nucleic acid sequence of SEQ ID NO: 4, 5, 6, 7 or 8.

Thus, in one aspect, the reverse primer comprises a nucleic acid sequence having at least 85%, preferably at least 90%, 91%, 92%, 93%, 94%, 95%, 96%, 97%, 98%, 99% and most preferably 100% sequence identity to a nucleic acid sequence of SEQ. ID NO: 10, 11, 12, 13 or 14.

Preferably, the forward primer consists of a nucleic acid sequence having at least 85%, preferably at least 90%, 91%, 92%, 93%, 94%, 95%, 96%, 97%, 98%, 99% and most preferably 100% sequence identity to a nucleic acid sequence of SEQ ID NO: 4, 5, 6, 7 or 8.

Preferably, the reverse primer consists of a nucleic acid sequence having at least 85%, preferably at least 90%, 91%, 92%, 93%, 94%, 95%, 96%, 97%, 98%, 99% and most preferably 100% sequence identity to a nucleic acid sequence of SEQ. ID NO: 10, 11, 12, 13 or 14.

An alternative means for defining variant primer sequences is by defining the number of nucleotides that differ between the variant sequence and the specific primer sequence. Thus, in one aspect, the variant primer sequences differ from SEQ ID NO: 4, 5, 6, 7, 8, 10, 11, 12, 13 or 14 at no more 3 nucleotide positions, preferably at no more than 2 nucleotide positions, most preferably at no more than 1 nucleotide position.

In one aspect, the step of amplifying the human papilloma virus nucleic acid comprises incorporation of a label into the amplicon.

In this regard, it is an option for at least one of the primers (preferably a reverse primer) to comprise a label (eg. at the 5' end of the primer) and, as amplification proceeds, the resulting amplicon will incorporate this label. The label enables detection and optionally quantification of the amplicon.

In this regard, the label may comprise a detectable molecule, such as a fluorescent molecule (eg. R-phycoerythrin). Alternatively, the label may comprise an attachment molecule, such as biotin, in which case the method may further comprise contacting said first attachment molecule with a reporter construct comprising a second attachment molecule that binds to the first attachment molecule, wherein said reporter construct comprises a detectable molecule, such as a fluorescent molecule.

In one aspect, the detection method comprises contacting said sample with multiple (ie. at least two) different forward primers and multiple (ie. at least two) different reverse primers that bind to target sites in the human papillomavirus L1 gene, or the complement thereof. In this regard, the forward primers differ from each other because they comprise a different nucleic acid sequence. Likewise, the reverse primers differ from each other because they comprise a different nucleic acid sequence.

In one aspect, each of said different forward primers comprises a different nucleic acid sequence selected from SEQ ID NO: 4, SEQ ID NO: 5, SEQ ID NO: 6, SEQ ID NO: 7 or SEQ ID NO: 8 (or sequences having at least 85%, preferably at least 90%, preferably at least 95%, more preferably at least 97%, most preferably 100% sequence identity thereto), and each of said different reverse primers comprises a different nucleic acid sequence selected from SEQ ID NO: 10, SEQ ID NO: 11, SEQ ID NO: 12, SEQ ID NO: 13 or SEQ ID NO: 14 (or sequences having 85%, preferably at least 90%, preferably at least 95%, more preferably at least 97% sequence identity thereto).

In one aspect, a forward primer comprising SEQ ID NO: 4 (or a sequence having 85%, preferably at least 90%, preferably at least 95%, more preferably at least 97% sequence identity thereto) is used in combination with a reverse primer comprising a nucleic acid sequence selected from SEQ ID NOs: 10, 11 or 14 (or sequences having 85%, preferably at least 90%, preferably at least 95%, more preferably at least 97% sequence identity thereto) and optionally in combination with one or more different probes comprising a nucleic acid sequence selected from SEQ ID NOs: 17, 19, 24 or 33 (or sequences having 85%, preferably at least 90%, preferably at least 95% sequence identity thereto).

In one aspect, a forward primer comprising SEQ ID NO: 5 (or a sequence having 85%, preferably at least 90%, preferably at least 95%, more preferably at least 97% sequence identity thereto) is used in combination with a reverse primer comprising a nucleic acid sequence selected from SEQ ID NOs: 10, 11 or 13 (or sequences having 85%, preferably at least 90%, preferably at least 95%, more preferably at least 97% sequence identity thereto) and optionally in combination with one or more different probes comprising a nucleic acid sequence selected from SEQ ID NOs: 15, 16, 18, 23 or 26 (or sequences having 85%, preferably at least 90%, preferably at least 95% sequence identity thereto).

In one aspect, a forward primer comprising SEQ ID NO: 6 (or a sequence having 85%, preferably at least 90%, preferably at least 95%, more preferably at least 97% sequence identity thereto) is used in combination with a reverse primer comprising a nucleic acid sequence selected from SEQ ID NOs: 11 or 12 (or sequences having 85%, preferably at least 90%, preferably at least 95%, more preferably at least 97% sequence identity thereto) and optionally in combination with one or more different probes comprising a nucleic acid sequence selected from SEQ ID NOs: 22 or 28 (or sequences having 85%, preferably at least 90%, preferably at least 95% sequence identity thereto).

In one aspect, a forward primer comprising SEQ ID NO: 7 (or a sequence having 85%, preferably at least 90%, preferably at least 95%, more preferably at least 97% sequence identity thereto) is used in combination with a reverse primer comprising a nucleic acid sequence selected from SEQ ID NOs: 10, 12 or 13 (or sequences having 85%, preferably at least 90%, preferably at least 95%, more preferably at least 97% sequence identity thereto) and optionally in combination with one or more different probes comprising a nucleic acid sequence selected from SEQ ID NOs: 20, 21 or 34 (or sequences having 85%, preferably at least 90%, preferably at least 95% sequence identity thereto).

In one aspect, a forward primer comprising SEQ ID NO: 8 (or a sequence having 85%, preferably at least 90%, preferably at least 95%, more preferably at least 97% sequence identity thereto) is used in combination with a reverse primer comprising SEQ ID NO: 14 (or a sequence having 85%, preferably at least 90%, preferably at least 95%, more preferably at least 97% sequence identity thereto) and optionally in combination with a probe comprising SEQ ID NO: 27 (or a sequence having 85%, preferably at least 90%, preferably at least 95% sequence identity thereto).

Likewise, in one aspect, a reverse primer comprising SEQ ID NO: 10 (or a sequence having 85%, preferably at least 90%, preferably at least 95%, more preferably at least 97% sequence identity thereto) is used in combination with a forward primer comprising a nucleic acid sequence selected from SEQ ID NOs: 4, 5 or 7 (or sequences having 85%, preferably at least 90%, preferably at least 95%, more preferably at least 97% sequence identity thereto) and optionally in combination with one or more different probes comprising a nucleic acid sequence selected from SEQ ID NOs: 17, 18, 21 or 23 (or sequences having 85%, preferably at least 90%, preferably at least 95% sequence identity thereto).

In one aspect, a reverse primer comprising SEQ ID NO: 11 (or a sequence having 85%, preferably at least 90%, preferably at least 95%, more preferably at least 97% sequence identity thereto) is used in combination with a forward primer comprising a nucleic acid sequence selected from SEQ ID NOs: 4, 5 or 6 (or sequences having 85%, preferably at least 90%, preferably at least 95%, more preferably at least 97% sequence identity thereto) and optionally in combination with one or more different probes comprising a nucleic acid sequence selected from SEQ ID NOs: 15, 22 or 24 (or sequences having 85%, preferably at least 90%, preferably at least 95% sequence identity thereto).

In one aspect, a reverse primer comprising SEQ ID NO: 12 (or a sequence having 85%, preferably at least 90%, preferably at least 95%, more preferably at least 97% sequence identity thereto) is used in combination with a forward primer comprising a nucleic acid sequence selected from SEQ ID NOs: 6 or 7 (or sequences having 85%, preferably at least 90%, preferably at least 95%, more preferably at least 97% sequence identity thereto) and optionally in combination with one or more different probes comprising a nucleic acid sequence selected from SEQ ID NOs: 20 or 28 (or sequences having 85%, preferably at least 90%, preferably at least 95% sequence identity thereto).

In one aspect, a reverse primer comprising SEQ ID NO: 13 (or a sequence having 85%, preferably at least 90%, preferably at least 95%, more preferably at least 97% sequence identity thereto) is used in combination with a forward primer comprising a nucleic acid sequence selected from SEQ ID NOs: 5 or 7 (or sequences having 85%, preferably at least 90%, preferably at least 95%, more preferably at least 97% sequence identity thereto) and optionally in combination with one or more different probes comprising a nucleic acid sequence selected from SEQ ID NOs: 26 or 34 (or sequences having 85%, preferably at least 90%, preferably at least 95% sequence identity thereto).

In one aspect, a reverse primer comprising SEQ ID NO: 14 (or a sequence having 85%, preferably at least 90%, preferably at least 95%, more preferably at least 97% sequence identity thereto) is used in combination with a forward primer comprising a nucleic acid sequence selected from SEQ ID NOs: 4 or 8 (or sequences having 85%, preferably at least 90%, preferably at least 95%, more preferably at least 97% sequence identity thereto) and optionally in combination with one or more different probes comprising a nucleic acid sequence selected from SEQ ID NOs: 19, 27 or 33 (or sequences having 85%, preferably at least 90%, preferably at least 95% sequence identity thereto).

As discussed above, the present invention enables quantitative estimates of pathogen load to be determined. Determining HPV load has many useful applications, such as for clinical guidance and for determining therapy, for patient management and for assessing vaccine efficacy.

Thus, in one aspect, the present invention provides an in vitro method of quantitating human papillomavirus pathogen load in a sample of interest, comprising: (a) carrying out a detection method according to the present invention on said sample of interest; and (b) carrying out said method on a test sample of predetermined known human papillomavirus pathogen load; and (c) comparing the signal detected from the sample of interest with the signal detected from the test sample; and thereby quantitating human papillomavirus pathogen load in the sample of interest.

In another aspect, the present invention is useful for determining efficacy of a course of treatment over a period of time, for example a course of drug therapy, such as vaccine therapy.

Thus, in one aspect, the present invention provides an in vitro method of determining drug efficacy over the course of a period of drug therapy, comprising: (a) carrying out a detection method according to the present invention on a first sample obtained at a first time point within or prior to the period of drug therapy; (b) carrying out said method on one or more samples obtained at one or more later time points within or after the period of drug therapy; and (c) comparing the signal detected from the first sample with the signal detected from the one or more later samples; and thereby determining drug efficacy over the course of the period of drug therapy.

In another aspect, the present invention is useful for determining the efficacy of a vaccine against human papillomavirus. Thus, in one aspect, the present invention provides an in vitro method of determining the efficacy of a vaccine against human papillomavirus, comprising: (a) carrying out a detection method according to the present invention on a first sample obtained from a patient at a first time point prior to vaccination; (b) carrying out said method on a sample obtained from said patient at one or more later time points following challenge with human papillomavirus; and (c) comparing the results obtained from the first sample with the results obtained from the one or more later samples; and thereby determining vaccine efficacy.

In another aspect, the invention provides an in vitro method of typing human papillomavirus in a sample, comprising: (a) carrying out a method according to the present invention on said sample using one or more genotype-specific probes; and (b) identifying the probe or probes that have bound to the human papillomavirus nucleic acid.

The invention also provides reagents for use in the above-described methods of the present invention.

Hence, in one aspect, the invention provides a probe as described above for use in accordance with the present invention.

In one aspect, the invention provides a set of probes as described above for use in accordance with the present invention.

In one aspect, the invention provides a forward primer as described above for use in accordance with the invention. In another aspect, the invention provides a reverse primer as described above for use in accordance with the invention. In another aspect, the invention provides a primer set comprising forward and reverse primers as described above for use in a method according to the invention.

Also provided by the present invention is a kit for detecting human papillomavirus nucleic acid in a sample, comprising a probe or set of probes as described above. Optionally, the kit includes a forward primer as described above. Optionally, the kit includes a reverse primer as described above. Optionally the kit comprises a primer set (comprising forward and reverse primers as described above).

FIG. 1 illustrates data generated using a HPV genotyping assay according to one aspect of the present invention ('High Risk' genotypes only) as compared to the known Roche LineBlot assay.

The present invention is discussed in more detail by means of the Examples described below.

EXAMPLES

Example 1

HPV Genotyping Assay

Conjugation of Oligonucleotides to Luminex Microspheres

Remove reagents (0.1% SDS, Tween 20 and 0.1M MES) from the fridge and allow to adjust to room temperature. Re-suspend lyophilised probe by adding volume of pharmaceutical water equal to the 'nmol' concentration on the tube, to give a 1 mM stock concentration. Select bead set, disperse pellet, sonicate and vortex for 1 minute. Dispense $5.0 \times 10^6$ beads (of total $1.25 \times 10^7$) into 1.5 ml tube (equivalent to 400 µl of 1 ml total). Label tube with probe ID and Luminex bead region ID eg. HPV16 [01]. N.B. To test a new probe use 150 µl bead stock and add 300 µl of 0.1M MES for final re-suspension. Centrifuge at 10,000 rpm for 1 mins then remove supernatant, being careful not to remove the beads. Add 50 µl of 0.1M MES vortex and sonicate.

Add 0.2 nM of probe (i.e. 0.2 µl of a 1 mM solution) and vortex briefly. This will give a probe concentration of 8 µM in 50 µl.

Immediately before use, add 1.0 ml sterile water to 10 mg (0.01 g) of EDC powder (stored, desiccated in −20° C. freezer) and vortex until dissolved. Add 2.5 µl of the fresh EDC solution to the microspheres and vortex immediately. Incubate for 30 mins at room temp in the dark. Repeat with fresh EDC (for a total of two EDC additions).

Add 1.0 ml of Tween 20 (0.02% v/v) and vortex. Microcentrifuge beads at 10,000 rpm for 1 minute. Remove the supernatant, being careful not to disturb the pellet. Add 1.0 ml of SDS (0.1% w/v) and vortex. Microcentrifuge the beads at 10,000 rpm for 1 minute. Remove the supernatant, being careful not to disturb the pellet. Re-suspend the beads in 800 µl of 0.1 M MES (pH 4.5). Enumerate the beads using the 'fast-read' counting chamber. Vortex and sonicate the beads for 1 minute.

Pipette 10 µl into one segment of the chamber, place under the light microscope in MRU and count the four corners of the grid. (The total reading should be between 80 and 140 beads). Store protected from light at 2-8° C.

Preparation of Buffers 0.1 M MES: Add 4.88 g MES (2[N-Morpholino] Ethanesulphonic acid) to 250 ml Sigma water, then adjust pH to 4.5 by adding approx 5 drops 5N of NaOH and filter sterilise.

0.02% Tween 20: Add 50 µl of Tween 20 to 250 ml Sigma water then filter sterilise.

0.1% SDS: Add 2.5 ml SDS (Lauryl Sulfate 10% solution) to 250 ml Sigma water and filter sterilise.

PCR Amplification of HPV L1 Gene

The PCR master mix for one reaction (45 µl) is made using the Qiagen Hot Start PCR kit as follows:

| 10 x buffer | 5.0 µl |
|---|---|
| dNTP | 5.0 µl |
| Q solution | 5.0 µl |
| 5 x Forward Primer | 2.5 µl (so final conc = 500 nM) |
| 5 x Reverse Primer | 2.5 µl (so final conc = 500 nM) |
| Hot Start Taq polymerase | 0.5 µl |
| Molecular grade water | 4.5 µl |
| Total volume | 25.0 µl |

Add 5 µl DNA from each sample to be tested to PCR plate or tubes depending on numbers.

Place PCR plate or tubes in a thermal cycler with the following cycling parameters: 95° C./15 mins, followed by 8 cycles of 95° C./30 secs, 54° C./1 min and 72° C./45 secs ensuring that the annealing temperature decreases by 1.5° C. with each cycle. This is followed by 35 cycles of 95° C./30 secs, 42° C./1 min, 72° C./45 secs ° C. with a final extension of 72° C./7 mins then holding at 4° C.

An electrophoresis step using a 2% agarose gel can be included to check the PCR amplicon size and band intensity.

Protocol for Direct DNA Hybridisation Assays

1. Make up the multi-analyte (bead) solution in 1.5×TMAC (the volume of each bead set to add is based on the concentration of beads per µl as previously calculated).

2. Add 12 µl TE buffer to a PCR plate (Millipore), 5 µl biotin-labelled PCR product and 33 µl of the bead preparation to each well. Ensure that the product and bead solution are well mixed.

3. Transfer plate to a thermal cycler programmed with the following parameters: 95° C./5 mins followed by 53° C. for 15 mins. While the cycle is proceeding, transfer the Luminex gold block to the −20° C. freezer.

4. Remove the plate from the thermal cycler and transfer to the chilled block to 'snap freeze' for 1 min. Remove the plate from the block and centrifuge at 2250×g/3 mins aspirate the liquid by inverting the plate and gently centrifuging at 80×g/20 secs being careful not to lose any beads. Transfer the gold block to BioPlex/Luminex instrument, which is set to heat to 53° C.

5. Dilute the Streptavidin-R-phycoerythrin (S-PE) conjugate 1:1000 in 1×TMAC (calculate volume to make up by multiplying number of wells by 75 µl).

6. Add 70 µl 1:1000 diluted S-PE, resuspend the beads by shaking the plate for 20 secs then return to the thermal cycler and incubate at 53° C. for a further 5 mins.

7. Remove the plate from the thermal cycler and transfer to the preheated block in the BioPlex/Luminex instrument. Read on the BioPlex/Luminex instrument.

Protocol for Reading Assays on the Bio-Plex/Luminex

1. Ensure that the laser has been warmed up before use. If the machine has been switched on for more than 30 mins this will have been done automatically. If not performed previously, select the 'start up' option. The machine will prompt for the positioning of sterile water and 70% isopropanol in the MCV plate. The 'start up' process takes approx 4 mins.
2. Select the option 'open protocol' from the menu and open the file HPV.

From the menu, chose option 'select analytes' and 'add' the analytes that are under test in the assay. i.e. 16, 18 etc.

3. Define the template by clicking on the X (=unknown) and dragging the cursor over the wells under test. Include the appropriate number of blank wells, designated as 'B'.
4. Insert the microtitre plate using the 'eject/retract' button on the menu and press the 'run' button. The instrument will calculate a series of Mean Fluorescent Intensity (MFI) values for each bead/probe for each sample.
5. When the instrument has finished reading select the option to transfer the data to an excel file for analysis.

Data Analysis

1. The cut-off for the assay is set at 1500 MFI with a 'grey zone' between 1500 and 2000 MFI where the test should be repeated.
2. Ensure that all of the MFI values in the 'Blank' wells are <1000.
3. Any HPV genotype(s) present in the sample will give a MFI value >2000 MFI.

Results

Luminex HPV Genotyping Assay vs. Roche Line Blot

|  |  | Luminex | | |
|  |  | Positive | Negative | Total |
| --- | --- | --- | --- | --- |
| Roche Line Blot | Positive | 258* | 7 | 265 |
|  | Negative | 16 | 18 | 34 |
|  | Total | 274 | 25 | 299 |

*Where Roche Line Blot identified a single genotype and in addition, the Luminex assay identified an additional 62 genotypes in 51 of 258 samples.

The invention claimed is:

1. An in vitro method of detecting human papillomavirus nucleic acid in a sample, comprising:
   contacting said sample with forward and reverse oligonucleotide primers, wherein said primers bind to target sites in the human papillomavirus L1 gene, or the complement thereof, under conditions suitable to promote amplification of a portion of said human papillomavirus L1 gene or complement, thereby generating an amplicon;
   wherein said forward primer binds to a target site having the sequence SEQ ID NO: 1, and
   wherein said reverse primer binds to a target site having the sequence SEQ ID NO: 2;
   contacting said amplicon with a set of probes, wherein said set of probes comprises
   (i) a probe comprising a nucleic acid having at least 90% sequence identity to SEQ ID NO: 15;
   (ii) a probe comprising a nucleic acid having at least 90% sequence identity to SEQ ID NO: 16;
   (iii) a probe comprising a nucleic acid having at at least 90% sequence identity to SEQ ID NO: 17; and
   (iv) a probe comprising a nucleic acid having at at least 90% sequence identity to SEQ ID NO: 18; and
   detecting binding of said set of probes to said amplicon.

2. The method of claim 1, wherein said set of probes comprises:
   (i) a probe comprising a nucleic acid having the sequence SEQ ID NO: 15,
   (ii) a probe comprising a nucleic acid having the sequence SEQ ID NO: 16,
   (iii) a probe comprising a nucleic acid having the sequence SEQ ID NO: 17, and
   (iv) a probe comprising a nucleic acid having the sequence SEQ ID NO: 18.

3. The method of claim 1, wherein each probe of said set of probes is immobilised onto a different solid support or platform.

4. The method of claim 3, wherein said different solid supports or platforms are uniquely identifiable beads or microspheres.

5. The method of claim 4, wherein following detecting binding of said amplicon to said set of probes, said method further comprises sorting said beads or microspheres according to their unique identification.

6. The method of claim 1, wherein said forward primer comprises a nucleic acid having the sequence SEQ ID NO: 3.

7. The method of claim 6, wherein said forward primer comprises a nucleic acid having at least 85% sequence identity to a sequence selected from SEQ ID NO: 4, SEQ ID NO: 5, SEQ ID NO: 6, SEQ ID NO: 7 or SEQ ID NO: 8.

8. The method of claim 7 wherein said forward primer consists of a nucleic acid having a sequence selected from SEQ ID NO: 4, SEQ ID NO: 5, SEQ ID NO: 6, SEQ ID NO: 7 or SEQ ID NO: 8.

9. The method of claim 1, wherein said reverse primer comprises a nucleic acid having the sequence SEQ ID NO: 9.

10. The method of claim 9, wherein said reverse primer comprises a nucleic acid having at least 85% sequence identity to a sequence selected from SEQ ID NO: 10, SEQ ID NO: 11, SEQ ID NO: 12, SEQ ID NO: 13 or SEQ ID NO: 14.

11. The method of claim 1, wherein said set of probes further comprises at least one additional probe comprising a nucleic acid having at least 85% sequence identity to a sequence selected from the group consisting of: SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

12. An in vitro method of detecting human papillomavirus nucleic acid in a sample, comprising:
  contacting said sample with forward and reverse oligonucleotide primers, wherein said primers bind to target sites in the human papillomavirus L1 gene, or the complement thereof, under conditions suitable to promote amplification of a portion of said human papillomavirus L1 gene or complement, thereby generating an amplicon;
  contacting said amplicon with a set of probes;
  wherein said set of probes comprises
    (i) a probe comprising a nucleic acid having at least 90% sequence identity to SEQ ID NO: 15;
    (ii) a probe comprising a nucleic acid having at least 90% sequence identity to SEQ ID NO: 16;
    (iii) a probe comprising a nucleic acid having at at least 90% sequence identity to SEQ ID NO: 17; and
    (iv) a probe comprising a nucleic acid having at at least 90% sequence identity to SEQ ID NO: 18; and
  detecting binding of said set of probes to said amplicon.

13. The method of claim 12, wherein said set of probes further comprises at least one additional probe comprising a nucleic acid having at least 85% sequence identity to a sequence selected from the group consisting of: SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

14. The method of claim 12, wherein each probe of said set of probes is immobilised onto a different solid support or platform.

15. The method of claim 14, wherein said different solid supports or platforms are uniquely identifiable beads or microspheres.

16. The method of claim 15, wherein following detecting binding of said amplicon to said set of probes, said method further comprises sorting said beads or microspheres according to their unique identification.

17. The method of claim 12, wherein said set of probes comprises:
  (i) a probe comprising a nucleic acid having the sequence SEQ ID NO: 15,
  (ii) a probe comprising a nucleic acid having the sequence SEQ ID NO: 16,
  (iii) a probe comprising a nucleic acid having the sequence SEQ ID NO: 17, and
  (iv) a probe comprising a nucleic acid having the sequence SEQ ID NO: 18.

18. An in vitro method of detecting human papillomavirus nucleic acid in a sample, comprising:
  contacting said sample with a set of probes that bind to a target site within the human papillomavirus L1 gene, or the complement thereof;
  wherein said set of probes comprises
    (i) a probe comprising a nucleic acid having at least 90% sequence identity to SEQ ID NO: 15;
    (ii) a probe comprising a nucleic acid having at least 90% sequence identity to SEQ ID NO: 16;
    (iii) a probe comprising a nucleic acid having at at least 90% sequence identity to SEQ ID NO: 17; and
    (iv) a probe comprising a nucleic acid having at at least 90% sequence identity to SEQ ID NO: 18; and
  detecting binding of said set of probes to said target site.

19. The method of claim 18, wherein each probe of said set of probes is immobilised onto a different solid support or platform.

20. The method of claim 19, wherein said different solid supports or platforms are uniquely identifiable beads or microspheres.

21. The method of claim 20, wherein following binding of said set of probes to said target site, said method further comprises sorting said beads or microspheres according to their unique identification.

22. The method of claim 18, wherein said set of probes further comprises at least one additional probe comprising a nucleic acid having at least 85% sequence identity to a sequence selected from the group consisting of: SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

23. The method of claim 18, wherein said set of probes comprises:
  (i) a probe comprising a nucleic acid having the sequence SEQ ID NO: 15,
  (ii) a probe comprising a nucleic acid having the sequence SEQ ID NO: 16,
  (iii) a probe comprising a nucleic acid having the sequence SEQ ID NO: 17, and
  (iv) a probe comprising a nucleic acid having the sequence SEQ ID NO: 18.

24. A set of probes that bind to a target sequence within the human papillomavirus L1 gene, or the complement thereof;
  wherein said set of probes comprises:
    (i) a probe comprising a nucleic acid having at least 90% sequence identity to SEQ ID NO: 15;
    (ii) a probe comprising a nucleic acid having at least 90% sequence identity to SEQ ID NO: 16;
    (iii) a probe comprising a nucleic acid having at at least 90% sequence identity to SEQ ID NO: 17; and (iv) a probe comprising a nucleic acid having at at least 90% sequence identity to SEQ ID NO: 18, wherein each probe of said set of probes is immobilized onto a solid support or platform.

25. The set of probes of claim 24, further comprising at least one additional probe comprising a nucleic acid having at least 85% sequence identity to a sequence selected from the group consisting of: SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

26. The set of probes of claim 24, wherein each probe of said set of probes is immobilised onto a different solid support or platform.

27. The set of probes of claim 26, wherein said different solid supports or platforms are uniquely identifiable beads or microspheres.

28. The set of probes of claim 24, comprising:
  (i) a probe comprising a nucleic acid having the sequence SEQ ID NO: 15,
  (ii) a probe comprising a nucleic acid having the sequence SEQ ID NO: 16,
  (iii) a probe comprising a nucleic acid having the sequence SEQ ID NO: 17, and
  (iv) a probe comprising a nucleic acid having the sequence SEQ ID NO: 18.

* * * * *

UNITED STATES PATENT AND TRADEMARK OFFICE
CERTIFICATE OF CORRECTION

PATENT NO. : 8,741,568 B2  
APPLICATION NO. : 12/526462  
DATED : June 3, 2014  
INVENTOR(S) : Caroline Corless et al.

It is certified that error appears in the above-identified patent and that said Letters Patent is hereby corrected as shown below:

On The Title Page:

Item (73) Assignee:

Please delete "Health Protection Agency, Salisbury (GB)" and insert --The Secretary of State for Health, London (GB)--

In The Claims:

Col. 30, Line 48, please delete "at at" and insert --at--  
Col. 30, Line 51, please delete "at at" and insert --at--

Col. 31, Line 10, please delete "6," and insert --1,--  
Col. 31, Line 14, please delete "7" and insert --7,--  
Col. 31, Line 20, please delete "9," and insert --1,--  
Col. 31, Line 48, please delete "at at" and insert --at--  
Col. 31, Line 50, please delete "at at" and insert --at--

Col. 32, Line 25, please delete "at at" and insert --at--  
Col. 32, Line 27, please delete "at at" and insert --at--  
Col. 32, Line 66, please delete "at at" and insert --at--

Col. 33, Line 1, please delete "at at" and insert --at--

Signed and Sealed this  
First Day of March, 2016

Michelle K. Lee  
*Director of the United States Patent and Trademark Office*

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Consensus sequence for forward primer binding
      site
<220> FEATURE:
<221> NAME/KEY: misc_feature
<222> LOCATION: (3)..(3)
<223> OTHER INFORMATION: n is a, c, g, or t

<400> SEQUENCE: 1
cgngtbccdr wdttvttacc                                                    20

<210> SEQ ID NO 2
<211> LENGTH: 26
<212> TYPE: DNA
<213> ORGANISM: Artificial Sequence
<220> FEATURE:
<223> OTHER INFORMATION: Consensus sequence for reverse primer binding
      site

<400> SEQUENCE: 2
gartwtgahy trcartttrt dtttca                                             26

<210> SEQ ID NO 3
<211> LENGTH: 20
<212> TYPE: DNA
<213> ORGANISM: Artificial Sequence
<220> FEATURE:
<223> OTHER INFORMATION: Consensus sequence for forward primer
<220> FEATURE:
<221> NAME/KEY: misc_feature
<222> LOCATION: (3)..(3)
<223> OTHER INFORMATION: n is a, c, g, or t

<400> SEQUENCE: 3
gcncargghy whaayaatgg                                                    20
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<222> LOCATION: (3)..(3)
<223> OTHER INFORMATION: n is a, c, g, or t

<400> SEQUENCE: 4
gcncaggghc acattaatgg                                              20

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
gchcargghc ataacaatgg                                              20

<210> SEQ ID NO 6
<211> LENGTH: 21
<212> TYPE: DNA
<213> ORGANISM: Artificial Sequence
<220> FEATURE:
<223> OTHER INFORMATION: Forward primer

<400> SEQUENCE: 6
gcmcagggty cataataatg g                                            21

<210> SEQ ID NO 7
<211> LENGTH: 20
<212> TYPE: DNA
<213> ORGANISM: Artificial Sequence
<220> FEATURE:
<223> OTHER INFORMATION: Forward primer

<400> SEQUENCE: 7
gcmcaaggyc ataataatgg                                              20

<210> SEQ ID NO 8
<211> LENGTH: 20
<212> TYPE: DNA
<213> ORGANISM: Artificial Sequence
<220> FEATURE:
<223> OTHER INFORMATION: Forward primer

<400> SEQUENCE: 8
gctcagggtt taaacaatgg                                              20

<210> SEQ ID NO 9
<211> LENGTH: 26
<212> TYPE: DNA
<213> ORGANISM: Artificial Sequence
<220> FEATURE:
<223> OTHER INFORMATION: Consensus sequence for reverse primer

<400> SEQUENCE: 9
tgaaahayaa aytgyardtc awaytc                                       26

<210> SEQ ID NO 10
<211> LENGTH: 26
<212> TYPE: DNA
<213> ORGANISM: Artificial Sequence
```

```
<220> FEATURE:
<223> OTHER INFORMATION: Reverse primer

<400> SEQUENCE: 10
tgaaaaataa actgyaaatc atattc                                              26

<210> SEQ ID NO 11
<211> LENGTH: 26
<212> TYPE: DNA
<213> ORGANISM: Artificial Sequence
<220> FEATURE:
<223> OTHER INFORMATION: Reverse primer

<400> SEQUENCE: 11
tgaaawataa attgyaawtc atactc                                              26

<210> SEQ ID NO 12
<211> LENGTH: 26
<212> TYPE: DNA
<213> ORGANISM: Artificial Sequence
<220> FEATURE:
<223> OTHER INFORMATION: Reverse primer

<400> SEQUENCE: 12
tgaaamacaa actgtagwtc atattc                                              26

<210> SEQ ID NO 13
<211> LENGTH: 26
<212> TYPE: DNA
<213> ORGANISM: Artificial Sequence
<220> FEATURE:
<223> OTHER INFORMATION: Reverse primer

<400> SEQUENCE: 13
tgaaaaacaa aytgtaaktc atattc                                              26

<210> SEQ ID NO 14
<211> LENGTH: 26
<212> TYPE: DNA
<213> ORGANISM: Artificial Sequence
<220> FEATURE:
<223> OTHER INFORMATION: Reverse primer

<400> SEQUENCE: 14
tgaaawataa aytgyaaatc aaattc                                              26

<210> SEQ ID NO 15
<211> LENGTH: 21
<212> TYPE: DNA
<213> ORGANISM: Artificial Sequence
<220> FEATURE:
<223> OTHER INFORMATION: Probe

<400> SEQUENCE: 15
catcttccac atacaccaat t                                                   21

<210> SEQ ID NO 16
<211> LENGTH: 26
<212> TYPE: DNA
<213> ORGANISM: Artificial Sequence
<220> FEATURE:
<223> OTHER INFORMATION: Probe

<400> SEQUENCE: 16
cactaattca gattataagg aataca                                              26
```

```
<210> SEQ ID NO 17
<211> LENGTH: 21
<212> TYPE: DNA
<213> ORGANISM: Artificial Sequence
<220> FEATURE:
<223> OTHER INFORMATION: Probe

<400> SEQUENCE: 17
gccatatcta cttcagaaac t                                              21

<210> SEQ ID NO 18
<211> LENGTH: 21
<212> TYPE: DNA
<213> ORGANISM: Artificial Sequence
<220> FEATURE:
<223> OTHER INFORMATION: Probe

<400> SEQUENCE: 18
atttaagcag tatagcagac a                                              21

<210> SEQ ID NO 19
<211> LENGTH: 21
<212> TYPE: DNA
<213> ORGANISM: Artificial Sequence
<220> FEATURE:
<223> OTHER INFORMATION: Probe

<400> SEQUENCE: 19
aattgcaaac agtgatacta c                                              21

<210> SEQ ID NO 20
<211> LENGTH: 23
<212> TYPE: DNA
<213> ORGANISM: Artificial Sequence
<220> FEATURE:
<223> OTHER INFORMATION: Probe

<400> SEQUENCE: 20
gactttatgc acacaagtaa cta                                            23

<210> SEQ ID NO 21
<211> LENGTH: 21
<212> TYPE: DNA
<213> ORGANISM: Artificial Sequence
<220> FEATURE:
<223> OTHER INFORMATION: Probe

<400> SEQUENCE: 21
tgtagttgat acaacccgta g                                              21

<210> SEQ ID NO 22
<211> LENGTH: 22
<212> TYPE: DNA
<213> ORGANISM: Artificial Sequence
<220> FEATURE:
<223> OTHER INFORMATION: Probe

<400> SEQUENCE: 22
ctacctctat agagtcttcc at                                             22

<210> SEQ ID NO 23
<211> LENGTH: 21
<212> TYPE: DNA
<213> ORGANISM: Artificial Sequence
<220> FEATURE:
<223> OTHER INFORMATION: Probe

<400> SEQUENCE: 23
```

```
tgtgcctcta cacaaaatcc t                                                21
```

<210> SEQ ID NO 24
<211> LENGTH: 21
<212> TYPE: DNA
<213> ORGANISM: Artificial Sequence
<220> FEATURE:
<223> OTHER INFORMATION: Probe

<400> SEQUENCE: 24

```
gtttccccaa catttactcc a                                                21
```

<210> SEQ ID NO 25
<211> LENGTH: 21
<212> TYPE: DNA
<213> ORGANISM: Artificial Sequence
<220> FEATURE:
<223> OTHER INFORMATION: Probe

<400> SEQUENCE: 25

```
gataccacca ggaatacaaa c                                                21
```

<210> SEQ ID NO 26
<211> LENGTH: 22
<212> TYPE: DNA
<213> ORGANISM: Artificial Sequence
<220> FEATURE:
<223> OTHER INFORMATION: Probe

<400> SEQUENCE: 26

```
cactgaagta actaaggaag gt                                               22
```

<210> SEQ ID NO 27
<211> LENGTH: 22
<212> TYPE: DNA
<213> ORGANISM: Artificial Sequence
<220> FEATURE:
<223> OTHER INFORMATION: Probe

<400> SEQUENCE: 27

```
tattcctaat gtatacacac ct                                               22
```

<210> SEQ ID NO 28
<211> LENGTH: 21
<212> TYPE: DNA
<213> ORGANISM: Artificial Sequence
<220> FEATURE:
<223> OTHER INFORMATION: Probe

<400> SEQUENCE: 28

```
gatgcccgtg aaatcaatca a                                                21
```

<210> SEQ ID NO 29
<211> LENGTH: 21
<212> TYPE: DNA
<213> ORGANISM: Artificial Sequence
<220> FEATURE:
<223> OTHER INFORMATION: Probe

<400> SEQUENCE: 29

```
taaggaatat attaggcatg t                                                21
```

<210> SEQ ID NO 30
<211> LENGTH: 21
<212> TYPE: DNA
<213> ORGANISM: Artificial Sequence

```
-continued

<220> FEATURE:
<223> OTHER INFORMATION: Probe

<400> SEQUENCE: 30
tcactattag tactgtatct g                                           21

<210> SEQ ID NO 31
<211> LENGTH: 21
<212> TYPE: DNA
<213> ORGANISM: Artificial Sequence
<220> FEATURE:
<223> OTHER INFORMATION: Probe

<400> SEQUENCE: 31
acaacgtatg ccaactctaa t                                           21

<210> SEQ ID NO 32
<211> LENGTH: 21
<212> TYPE: DNA
<213> ORGANISM: Artificial Sequence
<220> FEATURE:
<223> OTHER INFORMATION: Probe

<400> SEQUENCE: 32
tgcacagaca ttcactccaa c                                           21

<210> SEQ ID NO 33
<211> LENGTH: 21
<212> TYPE: DNA
<213> ORGANISM: Artificial Sequence
<220> FEATURE:
<223> OTHER INFORMATION: Probe

<400> SEQUENCE: 33
gaggttaaaa aggaaagcac a                                           21

<210> SEQ ID NO 34
<211> LENGTH: 21
<212> TYPE: DNA
<213> ORGANISM: Artificial Sequence
<220> FEATURE:
<223> OTHER INFORMATION: Probe

<400> SEQUENCE: 34
cagaacagtt aagtaaatat g                                           21
```